(12) United States Patent
Inoue

(10) Patent No.: US 6,355,820 B1
(45) Date of Patent: Mar. 12, 2002

(54) CHIRAL MOLECULAR MAGNET AND MANUFACTURING METHOD OF THE SAME

(75) Inventor: Katsuya Inoue, Okazaki (JP)

(73) Assignee: Okazaki National Research Institutes, Okazaki (JP)

( * ) Notice: Subject to any disclaimer, the term of this patent is extended or adjusted under 35 U.S.C. 154(b) by 0 days.

(21) Appl. No.: 09/597,583

(22) Filed: Jun. 20, 2000

(30) Foreign Application Priority Data

Feb. 21, 2000 (JP) ........................................ 2000-042970

(51) Int. Cl.$^7$ ........................... C07F 19/00; C07F 11/00; C07F 13/00; C30B 21/02
(52) U.S. Cl. ........................... 556/28; 548/101; 548/422; 117/68
(58) Field of Search ........................... 556/28; 548/101, 548/402; 117/68

(56) References Cited

FOREIGN PATENT DOCUMENTS

| JP | 9-246044 | 9/1997 |
|---|---|---|
| JP | 10-32111 | 2/1998 |
| JP | 10-208924 | 8/1998 |

OTHER PUBLICATIONS

Ohkoshi et al., Inorganic Chemistry, vol. 36, No. 3, pp. 268–269 (1997).*
Siberchicot et al., Journal of Magnetism and Magnetic Materials, vol. 157/158, pp. 417–418 (1996).*
G. Wagniere, et al. "The Influence of a Static Magnetic Field on the Absorption Coefficient of a Chiral Molecule," Chemical Physics Letters, vol. 93, No. 1, Nov. 19, 1982, pp. 78–81.
L.D. Barron, et al. "Magneto–chiral Birefringence and Dichroism," Molecular Physics, vol. 51, No. 3, 1984, pp. 715–730.

* cited by examiner

*Primary Examiner*—Porfirio Nazario-Gonzalez
(74) *Attorney, Agent, or Firm*—Oblon, Spivak, McCelland, Maier & Neustadt, P.C.

(57) ABSTRACT

There is disclosed a chiral molecular magnet having characteristics exhibiting a monocrystal, a magnetic property, an optical activity, a transparent color and a relatively high transition temperature. This chiral molecular magnet is formed of a monocrystal represented by a general formula $[Mn(L)]_3[Cr(CN)_6]_2 \cdot 4H_2O$ (wherein L is optically active (R or S)-1,2-diamines and derivatives thereof or optically active (R or S)-1,3-diamines and derivatives thereof).

8 Claims, 5 Drawing Sheets

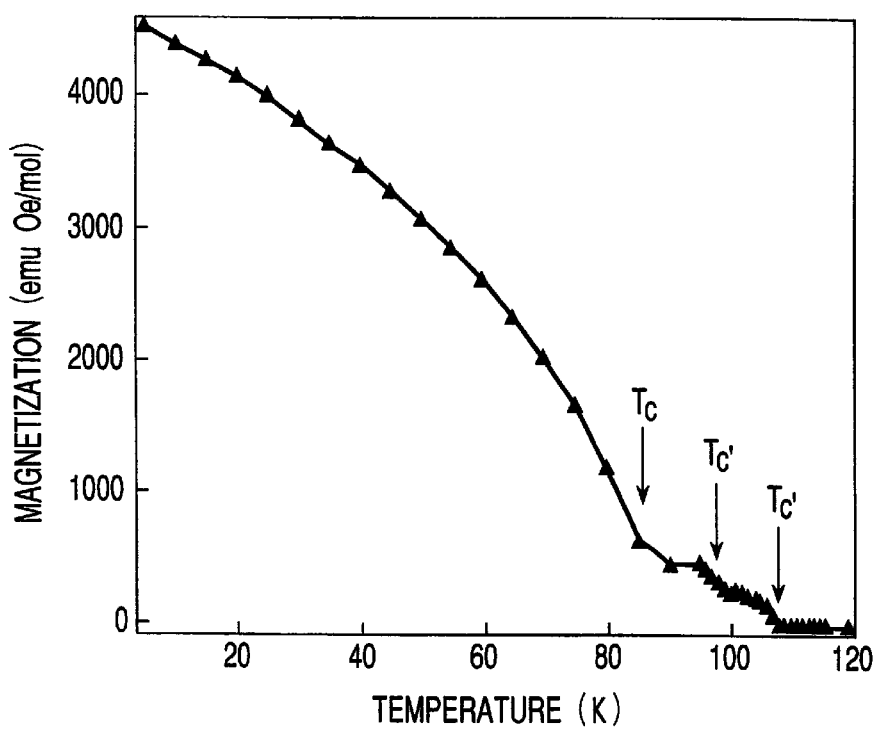
F I G. 7
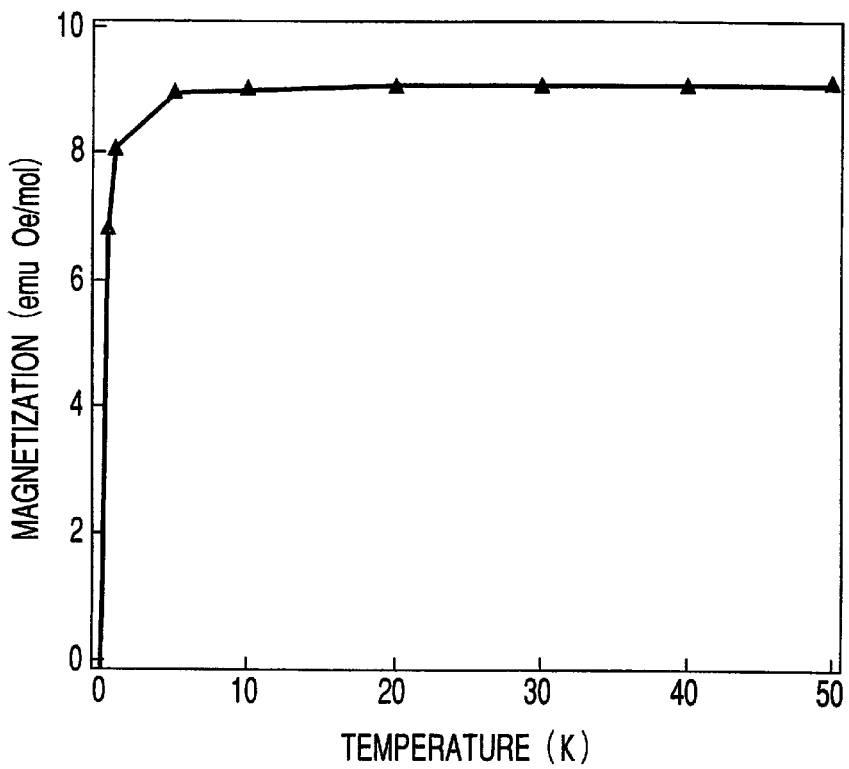
F I G. 8

# CHIRAL MOLECULAR MAGNET AND MANUFACTURING METHOD OF THE SAME

CROSS-REFERENCE TO RELATED APPLICATIONS

This application is based upon and claims the benefit of priority from the prior Japanese Patent Application No. 2000-042970, filed Feb. 21, 2000, the entire contents of which are incorporated herein by reference.

BACKGROUND OF THE INVENTION

This invention relates to a novel chiral molecular magnet, and also to a method of manufacturing such a chiral molecular magnet.

A phenomenon called "Magneto-Chiral Dichroism" has been known to occur in a chiral molecular magnet (magnetic material) as reported by G. Wagniere and A. Meier, "THE INFLUENCE OF STATIC MAGNETIC FIELD ON THE ABSORPTION COEFFICIENT OF A CHIRAL MOLECULE", Chemical Phys. Lett. Vol 93, pp.78–81 (1982); by G. Wagniere, Chemical Phys. Lett, Vol 110, pp.546–550(1984); and by L. D. BARRON, J. VRBANCICH, "Magneto-chiral birefringence and dichroism", Mol Phys., Vol.51, pp.715–730(1984). According to these publications, an actual substance is not referred to, but only theoretical studies are set forth therein. Namely, this "Magneto-Chiral Dichroism" is reported as being one kind of magneto-optical effect, exhibiting characteristics that the absorbency and luminous intensity of crystal can be controlled for instance by the direction of magnetization of crystal and by the advancing direction of light. Accordingly, since this optical characteristics can be controlled by the direction of magnetic field, versatile applications thereof are expected in various fields such as optical communication and optical technology.

Meanwhile, Japanese Patent Unexamined Publication H9-246044 discloses a molecular magnetic material comprising a cobalt-iron cyano complex exhibiting the characteristics that the magnetic property thereof can be altered by the irradiation of light, and that the magnetic property thereof after the irradiation of light can be varied by the changes in temperature.

Japanese Patent Unexamined Publication H10-32111 discloses a molecular mixed magnetic material comprising at least one kind of magnetic ion unit of molecular magnetic material exhibiting a ferromagnetism and at least one kind of magnetic ion unit of molecular magnetic material exhibiting a ferrimagnetism, which can be represented for example by $(Fe_{0.4}Mn_{0.6})_{1.6}Cr(CN)_6$, and whose magnetic property is variable by the irradiation of light.

Japanese Patent Unexamined Publication H10-208924 discloses a molecular magnetic material consisting for example of manganese(II)(tetraethoxyphenylporphyrin) tetracyanoethylene, and exhibiting a crystal magnetic anisotropy wherein the spin interaction in the direction of one-dimensional spin array is quite opposite to the spin interaction of an axis intersecting the aforementioned one-dimensional spin array.

BRIEF SUMMARY OF THE INVENTION

An object of the present invention is to provide a chiral molecular magnet having characteristics exhibiting a monocrystal, a magnetic property, an optical activity, a transparent color and a relatively high transition temperature.

Another object of the present invention is to provide a method which makes it possible to manufacture a chiral molecular magnet having a monocrystal of relatively large size and the aforementioned excellent properties at room temperature and with a high yield.

Namely, according to this invention, there is provided a chiral molecular magnet formed a monocrystal and represented by a general formula $[Mn(L)]_3[Cr(CN)_6]_2 \cdot 4H_2O$ (wherein L is optically active (R or S)-1,2-diamines and derivatives thereof or optically active (R or S)-1,3-diamines and derivatives thereof).

There is also provided a method of manufacturing a chiral molecular magnet, which comprises the steps of;

preparing a solution of a diamine compound by dissolving an optically active diamine compound selected from the group consisting of optically active (R or S)-1,2-diamines and derivatives thereof, and optically active (R or S)-1,3-diamine and derivatives thereof in a completely deaerated solvent under a non-oxidative atmosphere;

preparing a solution of manganate salt by dissolving manganate salt in a completely deaerated solvent under a non-oxidative atmosphere;

mixing the solution of a diamine compound with the solution of manganate salt under a non-oxidative atmosphere to obtain a mixed solution;

preparing a solution of hexacyanochromate salt by dissolving hexacyanochromate salt in a completely deaerated solvent under a non-oxidative atmosphere;

performing a reaction between the hexacyanochromate salt and the mixed solution by mixing the solution of hexacyanochromate salt with the mixed solution under a non-oxidative atmosphere to obtain a reaction mixture; and leaving the reaction mixture to stand at room temperature, thereby precipitating a monocrystal represented by a general formula $[Mn(L)]_3[Cr(CN)_6]_2 \cdot 4H_2O$ (wherein L is optically active (R or S)-1,2-diamines and derivatives thereof or optically active (R or S)-1,3-diamines and derivatives thereof).

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 7 is a graph showing the changes in magnetization in relative to the changes in temperature of the monocrystal (a chiral molecular magnet) obtained in Example 3 of the present invention;

FIG. 8 is a graph showing the changes in magnetic moment in relative to the changes in magnetic field at a temperature of 5K of the monocrystal (a chiral molecular magnet) obtained in Example 3 of the present invention.

DETAILED DESCRIPTION OF THE INVENTION

Figure 1:
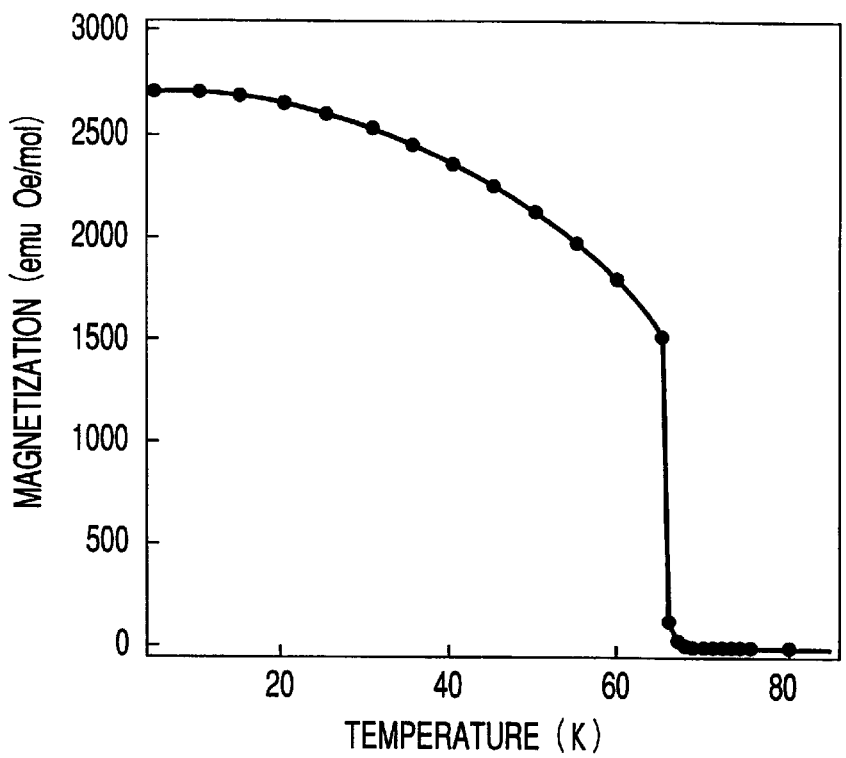
FIG. 1 is a graph showing the changes in magnetization in relative to the changes in temperature of the monocrystal (a chiral molecular magnet) obtained in Example 1 of the present invention.

Next, the present invention will be explained in detail as follows.

A chiral molecular magnet according to the present invention is formed of a monocrystal represented by a general formula $[Mn(L)]_3[Cr(CN)_6]_2 \cdot 4H_2O$ (wherein L is optically active (R or S)-1,2-diamines and derivatives thereof or optically active (R or S)-1,3-diamines and derivatives thereof).

As for the L in this general formula, compounds represented by the following structural formulas (1) to (31) can be employed:

(R)-alanamide, structural formula (1); (R,R)-1,2-diaminocyclohexane, structural formula (2); (R)-1,2-diaminopropane, structural formula (3); (L or R)-1,2-diaminobutane, structural formula (4); (L or R)-1,3-diaminobutane, structural formula (5); (L or R)-1,2-diaminobutan-1-one, structural formula (6); (L or R)-1,3-diaminobutan-2-one, structural formula (7); (L or R)-1,3-diaminobutan-1-one, structural formula (8); (S or R)-2-(aminomethyl) pyridine, structural formula (9); (1S,2S or 1R,2R)-N,N'-dimethyl-1,2-bis[3-(trifluoromethyl) phenyl]-1,2-ethanediamine, structural formula (10); dimethyl (1S,9S or 1R,9R)-5-cyanosemicorrin-1,9-dicarboxylate, structural formula (11); (1R,2R or 1S,2S)-1,2-diphenylethylenediamine, structural formula (12); (L or R) aspartate derivatives, structural formula (13); (L or R) aspartic acid derivatives, structural formula (14); (R or S) isoleucinamide, structural formula (15); (R or S) glutamide ester derivatives, structural formula (16); (R or S) cystenamide derivatives, structural formula (17); (R or S) serinamide derivatives, structural formula (18); (R or S) thyroxinamide derivatives, structural formula (19); (R or S) tyrosinamide derivatives, structural formula (20); (R or S) tryptophamide derivatives, structural formula (21); (R or S) threonamide derivatives, structural formula (22); (R or S) valinamide derivatives, structural formula (23); (R or S) histidinamide derivatives, structural formula (24); (R or S)-4-hydroxyprolinamide derivatives, structural formula (25); (R or S)-4-hydroxylysinamide derivatives, structural formula (26); (R or S) phenylalanamide, structural formula (27); (R or S) prolinamide, structural formula (28); (R or S) methionamide, structural formula (29); (R or S) lysinamide derivatives, structural formula (30); and (R or S) leucinamide, structural formula (31).

$R^1$ in the following structural formulas (13), (14), (16) to (20), (22), (25), (26) and (30) is hydrogen atom, or alkyl group such as methyl, ethyl, etc., and $R^2$ in the following structural formula (26) is hydrogen atom, or alkyl group such as methyl, ethyl, etc.

(1)
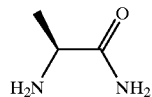

(2)
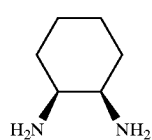

(3)
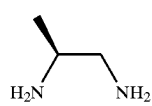

(4)
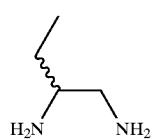

(5)
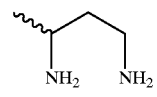

(6)
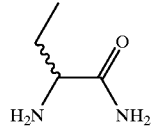

(7)
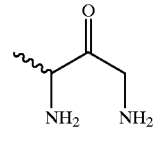

(8)
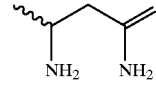

(9)

(10)
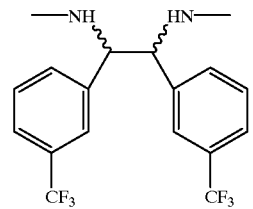

-continued

(11) (12) (13) (14) (15) (16) (17) (18) (19) (20) (21) (22) (23) (24) (25) (26) (27) (28) (29)

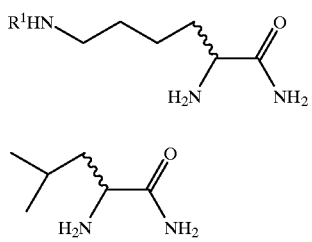

Next, a method of manufacturing a chiral molecular magnet according to this invention will be explained.

First of all, an optically active diamine compound selected from optically active (R or S)-1,2-diamines and derivatives thereof, and optically active (R or S)-1,3-diamine and derivatives thereof are dissolved in a completely deaerated solvent under a non-oxidative atmosphere, thereby preparing a solution of diamine compound.

As for the optically active diamine compound, it is possible to employ a compound having any one of the aforementioned structural formulas (1) to (31).

The non-oxidative atmosphere in this case means an atmosphere such as an argon gas, helium gas or nitrogen gas atmosphere.

The completely deaerated solvent useful in this case includes a completely deaerated pure water, a completely deaerated water-alcohol mixture, etc.

Thereafter, a solution of manganate salt is prepared by dissolving manganate salt in a completely deaerated solvent under a non-oxidative atmosphere, and then, this manganate salt solution is mixed with the aforementioned solution of a diamine compound under a non-oxidative atmosphere to prepare a mixed solution.

As for the manganate salt, it is possible to employ manganese chloride(II) hydrate or manganese perchlorate (II) hydrate.

The completely deaerated solvent useful in this case includes a completely deaerated pure water, a completely deaerated water-alcohol mixture, etc.

Then, a solution of hexacyanochromate salt is prepared by dissolving hexacyanochromate salt in a completely deaerated solvent under a non-oxidative atmosphere. Thereafter, this solution of hexacyanochromate salt is mixed with the aforementioned mixed solution under a non-oxidative atmosphere to perform a reaction between the hexacyanochromate salt and the mixed solution, thereby obtaining a reaction mixture. This reaction mixture is then left to stand at room temperature, thereby allowing to precipitate a monocrystal represented by a general formula $[Mn(L)]_3[Cr(CN)_6]_2 \cdot 4H_2O$ (wherein L is optically active (R or S)-1,2-diamines and derivatives thereof or optically active (R or S)-1,3-diamines and derivatives thereof), thus manufacturing a chiral molecular magnet.

As for the hexacyanochromate salt, it is possible to employ potassium hexacyanochromate, sodium hexacyanochromate, ammonium hexacyanochromate, etc.

The completely deaerated solvent useful in this case includes a completely deaerated pure water, a completely deaerated water-alcohol mixture, etc.

As explained above, since the chiral molecular magnet according to the present invention is formed of a monocrystal (cubic system) represented by a general formula $[Mn(L)]_3[Cr(CN)_6]_2 \cdot 4H_2O$ (wherein L is optically active (R or S)-1,2-diamines and derivatives thereof or optically active (R or S)-1,3-diamines and derivatives thereof), the molecular magnet will exhibit the following features.

(1) It has an asymmetric optical structure exhibiting an optical activity (circular dichroism) due to the incorporation of L in the aforementioned general formula.

(2) It exhibits a molecularity.

(3) It is transparent (transparent color) and monocrystal.

(4) It exhibits a relatively high transition temperature (for example, 108K).

The chiral molecular magnet of the present invention having such characteristics can be used for instance for the conversion of wavelength of light through a magnetic field, for the control of intensity of light absorbency, and for the control of rotation of photo-oscillation vector, so that it is applicable for instance to a photoelectro-magnetic device, a magnetic field responsive optical device, a magnetic field responsive optical crystal, and an optical communication device.

Further, according to the method of this invention, a chiral molecular magnet having a monocrystal of relatively large size and the aforementioned excellent properties can be manufactured at room temperature and with a high yield.

Next, preferable examples of this invention will be explained in detail.

EXAMPLE 1

First of all, a 30 mL Kjeldahl flask was filled with 0.2 m mole of (R)-alanamide having the aforementioned structure (1) under an argon atmosphere. Then, 3 mL of a completely deaerated pure water was poured into this flask under an argon atmosphere, thereby completely dissolving the (R)-alanamide in the pure water to obtain a solution of (R)-alanamide.

Then, 0.2 millimole of manganese perchlorate(II) hydrate was added to and dissolved in 7 mL of a completely deaerated pure water under an argon atmosphere to obtain a solution of manganese perchlorate. The solution of manganese perchlorate obtained was then added to and mixed with the (R)-alanamide filled in the flask under an argon atmosphere to prepare a mixed solution. Thereafter, 0.2 millimole of potassium hexacyanochromate was added to and dissolved in 5 mL of a completely deaerated pure water under an argon atmosphere to obtain a solution of potassium hexacyanochromate. The solution of potassium hexacyanochromate was then added to and mixed with the mixed solution filled in the to perform a reaction between the potassium hexacyanochromate and the mixed solution, thereby obtaining a reaction solution. The resultant solution was left to stand for a whole day and night at room temperature to precipitate a monocrystal.

The monocrystal thus obtained was found as being a transparent yellow cubic system crystal 8 mm in diameter and having a formula of:

$[Mn(L)]_3[Cr(CN)_6]_2 \cdot 4H_2O$ (wherein L is (R)-alanamide).

The yield of this monocrystal was 88% based on the raw material.

Then, this monocrystal (chiral molecular magnet) obtained in this example was assessed with respect to the magnetic property and optical activity thereof.

1) Temperature-magnetization property

A sample having a dimension of: 0.8 mm×0.8 mm×0.8 mm and cut out of this monocrystal was placed in a magnetic field of 5 Oe to measure the changes of magnetization as the temperature thereof was varied by making use of a SQUID flux meter, the results being shown in FIG. 1.

As apparent from FIG. 1, when temperature becomes lower than about 70K, the magnetization of the monocrystal (chiral molecular magnet) of this example 1 was sharply increased, thus confirming that this monocrystal exhibited ferrimagnetism at this temperature zone.

2) Magnetic field dependency of magnetic moment

Figure 2:
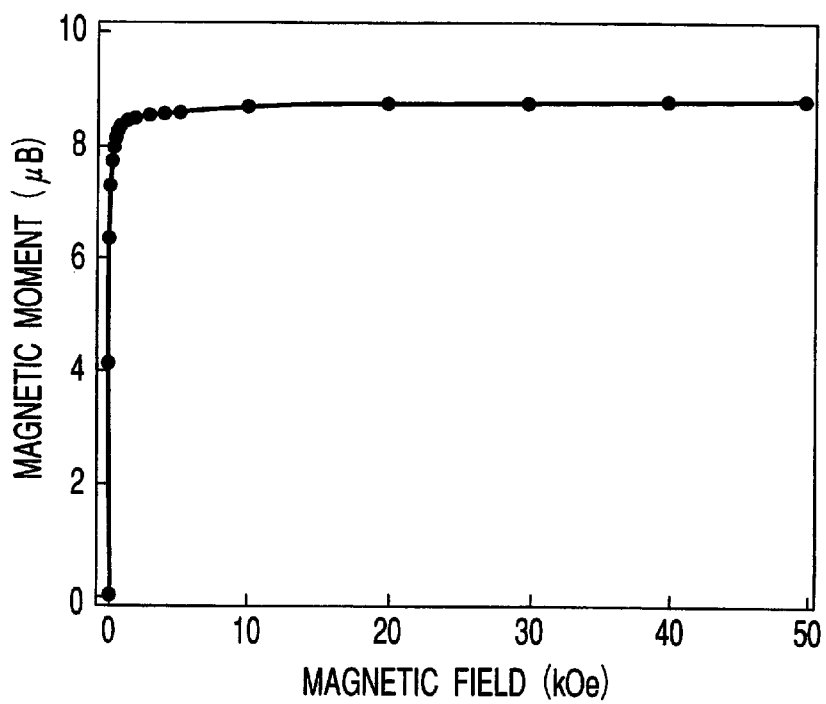
FIG. 2 is a graph showing the changes in magnetic moment in relative to the changes in magnetic field at a temperature of 5K of the monocrystal (a chiral molecular magnet) obtained in Example 1 of the present invention.

A sample having a dimension of: 0.8 mm×0.8 mm×0.8 mm and cut out of this monocrystal was left to stand under an atmosphere of 5K in temperature to measure the changes of magnetic moment as the magnetic field was varied by making use of a SQUID flux meter, the results being shown in FIG. 2.

As apparent from FIG. 2, it was possible to confirm the magnetism of the monocrystal (chiral molecular magnet) of this example 1 from the fact that the magnetic moment of this monocrystal at a temperature of 5K was saturated at about 100 Oe. Further, from the fact that the value of the saturated magnetic moment was about 9 $\mu$B, it was possible to confirm that the magnetization of chromium and manganese which were constituent components of the chiral molecular magnet was arrayed 100%.

Figure 3:
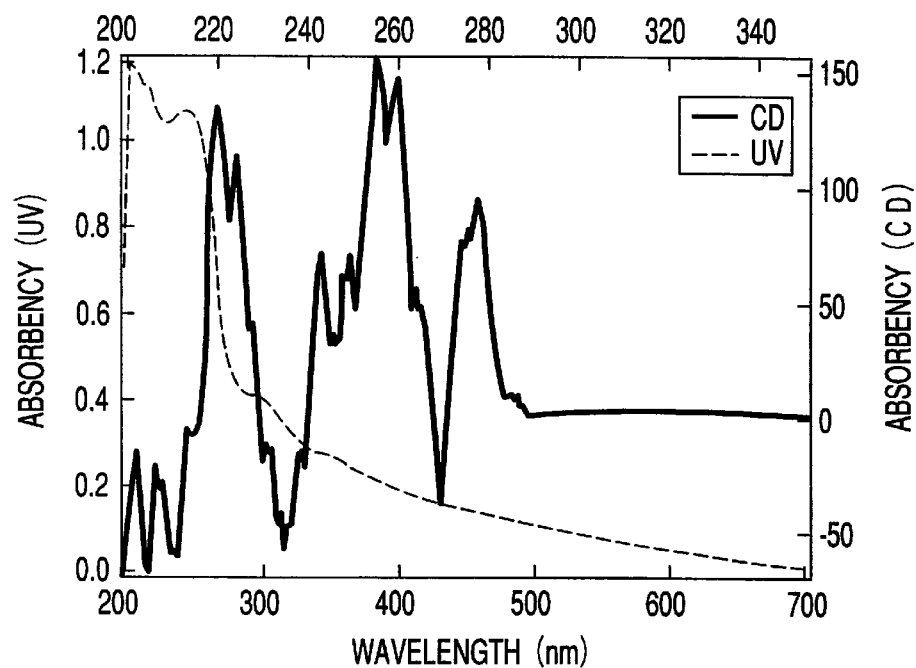
FIG. 3 is a graph showing the light absorption spectrum (CD and UV) of the monocrystal (a chiral molecular magnet) obtained in Example 1 of the present invention.

3) CD (circular dichroism) absorption spectrum and ultraviolet ray absorption spectrum A sample having a dimension of: 2.0 mm×2.0 mm×0.5 mm and cut out of this monocrystal was employed to measure the light absorption spectrum (CD and UV) of this monocrystal by allowing light of varied wavelength to pass therethrough at room temperature by making use of a circular dichromatism spectrometer and a spectrophotometer respectively, the results being shown in FIG. 3. By the way, the light absorption spectrum of UV is denoted by the lower abscissa and the left ordinate in FIG. 3, while the light absorption spectrum of DC is denoted by the upper abscissa and the right ordinate in FIG. 3.

As seen from FIG. 3, from the fact that the light absorption spectrum of CD was not zero at a prescribed wavelength zone in the monocrystal (chiral molecular magnet) of this example 1, it was suggested that this monocrystal was optically active.

EXAMPLE 2

First of all, a 30 mL Kjeldahl flask was filled with 0.2 m mole of (R,R)-1,2-diaminocyclohexane having the aforementioned structure (2) under an argon atmosphere. Then, 3 mL of a completely deaerated pure water was poured into this flask under an argon atmosphere, thereby completely dissolving (R,R)-1,2-diaminocyclohexane in the pure water to obtain a solution of (R,R)-1,2-diaminocyclohexane.

Then, 0.2 millimole of manganese perchlorate(II) hydrate was added to and dissolved in 7 mL of a completely deaerated pure water under an argon atmosphere to obtain a solution of manganese perchlorate. The solution of manganese perchlorate obtained was then added to and mixed with the (R,R)-1,2-diaminocyclohexane filled in the flask under an argon atmosphere to prepare a mixed solution. Thereafter, 0.2 millimole of potassium hexacyanochromate was added to and dissolved in 5 mL of a completely deaerated pure water under an argon atmosphere to obtain a solution of potassium hexacyanochromate. The solution of potassium hexacyanochromate obtained was then added to and mixed with the mixed solution filled in the flask under an argon atmosphere to perform a reaction between the potassium hexacyanochromate and the mixed solution, thereby obtaining a reaction solution. The resultant solution was left to stand for a whole day and night at room temperature to precipitate a monocrystal.

The monocrystal thus obtained was found as being a transparent yellow cubic system crystal 8 mm in diameter and having a formula of: [Mn(L)]$_3$[Cr(CN)$_6$]$_2$.4H$_2$O (wherein L is (R,R)-1,2-diaminocyclohexane). The yield of this monocrystal was 88% based on the raw material.

Then, this monocrystal (chiral molecular magnet) obtained in this example 2 was assessed with respect to the magnetic property and optical activity thereof.

1) Temperature-magnetization property

Figure 4:
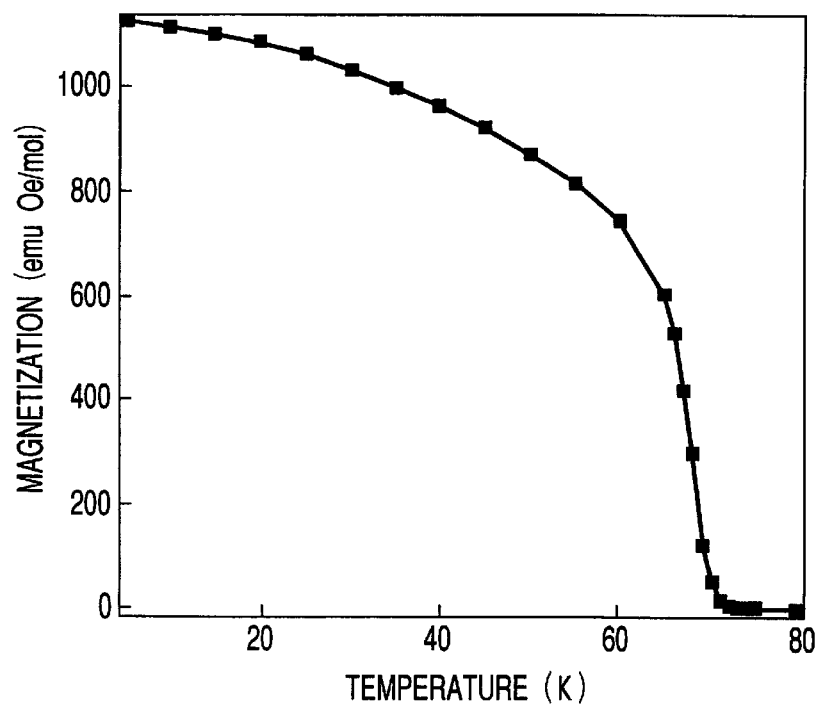
FIG. 4 is a graph showing the changes in magnetization in relative to the changes in temperature of the monocrystal (a chiral molecular magnet) obtained in Example 2 of the present invention.

The changes of magnetization in relative to the changes in temperature of this monocrystal were measured in the same manner as illustrated in Example 1, the results being shown in FIG. 4.

As apparent from FIG. 4, when temperature becomes lower than about 72K, the magnetization of the monocrystal (chiral molecular magnet) of this example 2 was sharply increased, thus confirming that this monocrystal exhibited ferrimagnetism at this temperature zone.

2) Magnetic field dependency of magnetic moment

Figure 5:
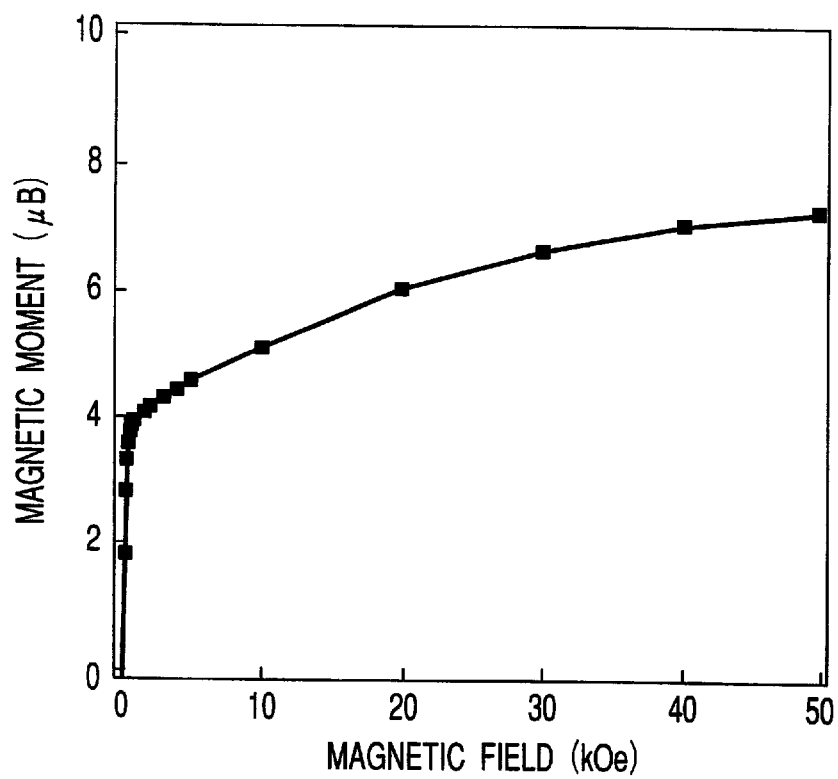
FIG. 5 is a graph showing the changes in magnetic moment in relative to the changes in magnetic field at a temperature of 5K of the monocrystal (a chiral molecular magnet) obtained in Example 2 of the present invention.

In the same manner as illustrated in Example 1, the changes of magnetic moment of this monocrystal in relative to the changes in magnetic field at a temperature of 5K were measured, the results being shown in FIG. 5.

As apparent from FIG. 5, it was possible to confirm the magnetism of the monocrystal (chiral molecular magnet) of this example 2 from the fact that the magnetic moment of this monocrystal at a temperature of 5K was saturated at about 100 Oe. Further, from the fact that the value of the saturated magnetic moment was about 7 $\mu$B, it was possible to confirm that the magnetization of chromium and manganese which were constituent components of the chiral molecular magnet was arrayed 100%.

3) CD (circular dichroism) absorption spectrum

Figure 6:
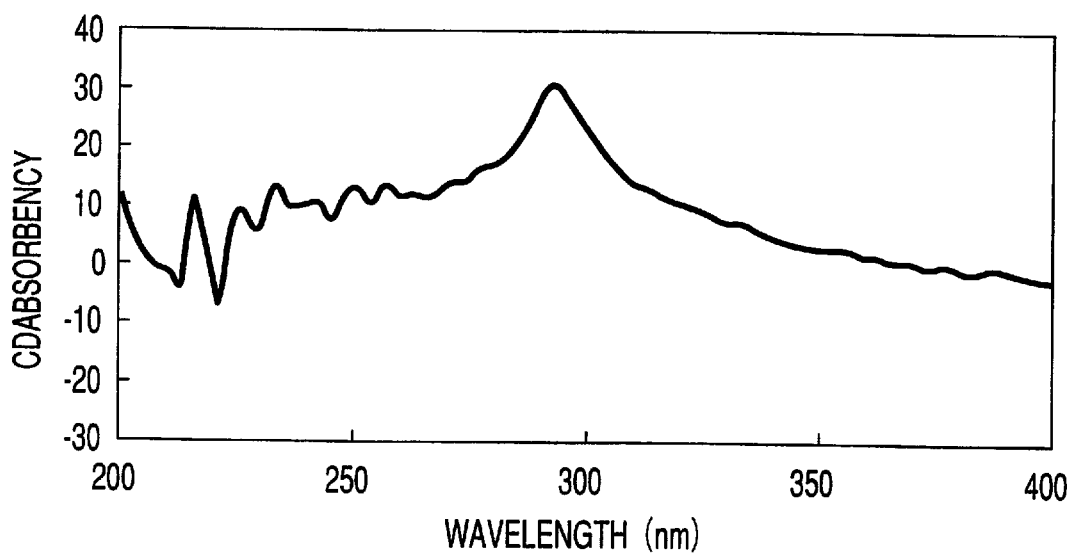
FIG. 6 is a graph showing the light absorption spectrum (CD and UV) of the monocrystal (a chiral molecular magnet) obtained in Example 2 of the present invention.

In the same manner as illustrated in Example 1, the light absorption spectrum (CD) of this monocrystal was measured, the results being shown in FIG. 6.

As seen from FIG. 6, from the fact that the light absorption spectrum of CD was not zero at a prescribed wavelength zone in the monocrystal (chiral molecular magnet) of this example 2, it was suggested that this monocrystal was optically active.

EXAMPLE 3

First of all, a 30 mL Kjeldahl flask was filled with 0.2 m mole of (R)-1,2-diaminopropane having the aforementioned structure (3) under an argon atmosphere. Then, 3 mL of a completely deaerated pure water was poured into this flask under an argon atmosphere, thereby completely dissolving (R)-1,2-diaminopropane in the pure water to obtain a solution of (R)-1,2-diaminopropane.

Then, 0.2 millimole of manganese perchlorate(II) hydrate was added to and dissolved in 7 mL of a completely deaerated pure water under an argon atmosphere to obtain a solution of manganese perchlorate. The solution of manganese perchlorate obtained was then added to and mixed with the (R)-1,2-diaminopropane filled in the flask under an argon atmosphere to prepare a mixed solution. Thereafter, 0.2 millimole of potassium hexacyanochromate was added to and dissolved in 5 mL of a completely deaerated pure water under an argon atmosphere to obtain a solution of potassium hexacyanochromate. The solution of potassium hexacyanochromate obtained was then added to and mixed with the mixed solution filled in the flask under an argon atmosphere to perform a reaction between the potassium hexacyanochromate and the mixed solution, thereby obtaining a reaction solution. The resultant solution was left to stand for a whole day and night at room temperature to obtain a monocrystal to be precipitated.

The monocrystal thus obtained was found as being a transparent green cubic system crystal 8 mm in diameter and having a formula of:

$[Mn(L)]_3[Cr(CN)_6]_2 \cdot 4H_2O$ (wherein L is (R)-1,2-diaminopropane). The yield of this monocrystal was 88% based on the raw material.

Then, this monocrystal (chiral molecular magnet) obtained in this example 3 was assessed with respect to the magnetic property and optical activity thereof.

1) Temperature-magnetization property

The changes of magnetization in relative to the changes in temperature of this monocrystal were measured in the same manner as illustrated in Example 1, the results being shown in FIG. 7.

As apparent from FIG. 7, when temperature becomes lower than about 108K, the magnetization of the monocrystal (chiral molecular magnet) of this example 3 was sharply increased, thus confirming that this monocrystal exhibited ferrimagnetism at this temperature zone. Further, from the fact that the magnetization of this monocrystal was sharply increased at about 100K and at about 90K, it was recognized that this monocrystal included crystals exhibiting a transition temperature of about 100 or about 90K.

2) Magnetic field dependency of magnetic moment

In the same manner as illustrated in Example 1, the changes of magnetic moment of this monocrystal in relative to the changes in magnetic field at a temperature of 5K were measured, the results being shown in FIG. 8.

As apparent from FIG. 8, it was possible to confirm the magnetism of the monocrystal (chiral molecular magnet) of this example 3 from the fact that the magnetic moment of this monocrystal at a temperature of 5K was saturated at about 100 Oe. Further, from the fact that the value of the saturated magnetic moment was about 9 $\mu B$, it was possible to confirm that the magnetization of chromium and manganese which were constituent components of the chiral molecular magnet was arrayed 100%.

3) CD (circular dichroism) absorption spectrum

Figure 9:
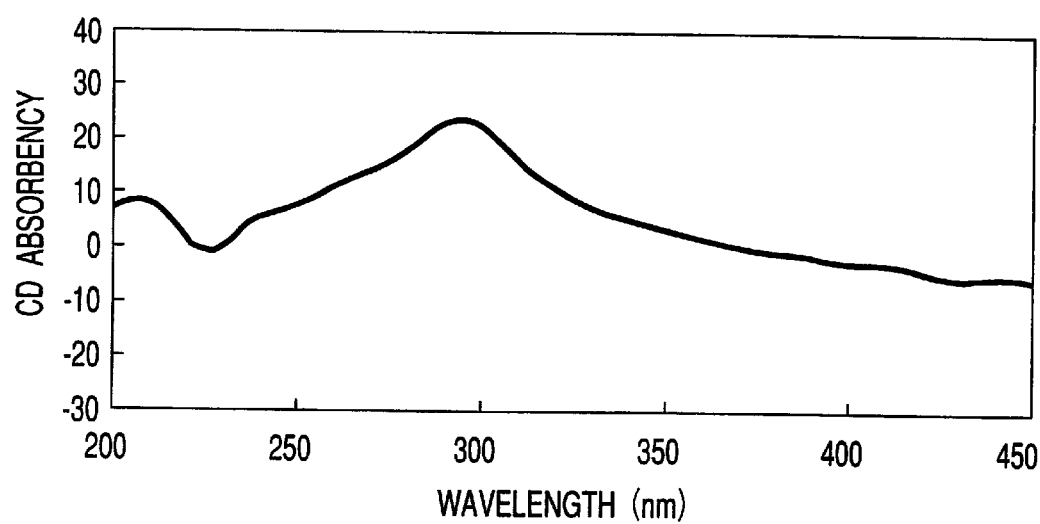
FIG. 9 is a graph showing the light absorption spectrum (CD and UV) of the monocrystal (a chiral molecular magnet) obtained in Example 3 of the present invention.

In the same manner as illustrated in Example 1, the light absorption spectrum (CD) of this monocrystal was measured, the results being shown in FIG. 9.

As seen from FIG. 9, from the fact that the light absorption spectrum of CD was not zero at a prescribed wavelength zone in the monocrystal (chiral molecular magnet) of this example 3, it was suggested that this monocrystal was optically active.

As explained above, it is possible according to the present invention to provide a monocrystalline chiral molecular magnet, which exhibits a magnetism and an optical activity, and has a transparent color and an excellent property such as a relatively high transition temperature, so that it can be applied to a photoelectro-magnetic device, a magnetic field responsive optical device, a magnetic field responsive optical crystal, and an optical communication device.

Further, according to the method of the present invention, it is possible to manufacture a monocrystalline chiral molecular magnet of relatively large size and having the aforementioned excellent properties at room temperature and with a high yield.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A chiral molecular magnet formed a monocrystal and represented by a general formula $[Mn(L)]_3[Cr(CN)_6]_2 \cdot 4H_2O$ (wherein L is optically active (R or S)-1,2-diamines and derivatives thereof or optically active (R or S)-1,3-diamines and derivatives thereof).

2. The chiral molecular magnet according to claim 1, wherein L in said general formula is optically active (S)-alanamide.

3. The chiral molecular magnet according to claim 1, wherein L in said general formula is optically active (R,R)-1,2-diaminocyclohexane.

4. The chiral molecular magnet according to claim 1, wherein L in said general formula is optically active (R)-1,2-diaminopropane.

5. A method of manufacturing a chiral molecular magnet, which comprises the steps of;

preparing a solution of a diamine compound by dissolving an optically active diamine compound selected from the group consisting of optically active (R or S)-1,2-diamines and derivatives thereof, and optically active (R or S)-1,3-diamine and derivatives thereof in a completely deaerated solvent under a non-oxidative atmosphere;

preparing a solution of manganate salt by dissolving manganate salt in a completely deaerated solvent under a non-oxidative atmosphere;

mixing said solution of a diamine compound with the solution of manganate salt under a non-oxidative atmosphere to obtain a mixed solution;

preparing a solution of hexacyanochromate salt by dissolving hexacyanochromate salt in a completely deaerated solvent under a non-oxidative atmosphere;

performing a reaction between the hexacyanochromate salt and the mixed solution by mixing the solution of hexacyanochromate salt with the mixed solution under a non-oxidative atmosphere to obtain a reaction mixture; and leaving the reaction mixture to stand at room temperature, thereby precipitating a monocrystal represented by a general formula $[Mn(L)]_3[Cr(CN)_6]_2 \cdot 4H_2O$ (wherein L is optically active (R or S)-1,2-diamines and derivatives thereof or optically active (R or S)-1,3-diamines and derivatives thereof).

6. The method of manufacturing a chiral molecular magnet according to claim 5, wherein said completely deaerated solvent is a completely deaerated pure water.

7. The method of manufacturing a chiral molecular magnet according to claim 5, wherein said manganate is manganese chloride(II) hydrate or manganese perchlorate(II) hydrate.

8. The method of manufacturing a chiral molecular magnet according to claim 5, wherein said hexacyanochromate is potassium hexacyanochromate.

* * * * *